United States Patent
Viertiö-Oja et al.

(10) Patent No.: US 8,145,297 B2
(45) Date of Patent: Mar. 27, 2012

(54) MEASUREMENT OF EEG REACTIVITY

(75) Inventors: Hanna E. Viertiö-Oja, Espoo (FI); Mika Särkelä, Helsinki (FI); Juha Virtanen, Helsinki (FI); Tapani Salmi, Vantaa (FI)

(73) Assignee: General Electric Company, Schenectady, NY (US)

( * ) Notice: Subject to any disclaimer, the term of this patent is extended or adjusted under 35 U.S.C. 154(b) by 1588 days.

(21) Appl. No.: 11/523,789

(22) Filed: Sep. 19, 2006

(65) Prior Publication Data

US 2007/0179399 A1    Aug. 2, 2007

Related U.S. Application Data

(63) Continuation-in-part of application No. 11/273,574, filed on Nov. 14, 2005, now Pat. No. 8,064,993.

(51) Int. Cl.
*A61B 5/04* (2006.01)
(52) U.S. Cl. ...................................... 600/544
(58) Field of Classification Search ................. 600/544, 600/559
See application file for complete search history.

(56) References Cited

U.S. PATENT DOCUMENTS

| | | | |
|---|---|---|---|
| 5,230,344 A | 7/1993 | Ozdamar et al. |
| 6,236,885 B1 | 5/2001 | Hunter et al. |
| 6,256,531 B1 | 7/2001 | Ilmoniemi et al. |
| 6,731,975 B1 | 5/2004 | Viertio-Oja et al. |
| 6,868,345 B1 | 3/2005 | Jensen |
| 2003/0004429 A1 | 1/2003 | Price |
| 2003/0073921 A1 | 4/2003 | Sohmer et al. |

FOREIGN PATENT DOCUMENTS

WO    98/10701 A1    3/1998

OTHER PUBLICATIONS

Electroencephalography, Basic Principles, Clinical Applications, and Related Fields, E. Niedermeyer, M.D. et al., Lippincott Williams & Wilkins, Fourth Edition, 1999, p. 462.
An Electroencephalographic Classification for Coma, G. B. Young, et al., The Canadian Journal of Neurological Sciences, 1997; 24: 320-325.
European Search Report dated Jan. 29, 2008.
Anderson et al., "Entropy during propofol hypnosis, including an episode of wakefulness", Anaesthesia, Jan. 2004, vol. 52, pp. 52-56, Blackwell Publishing Ltd.
Young et al., "An Electroencephalographic Classification for Coma", Canadian Journal of Neurological Sciences, Nov. 1997, vol. 24, pp. 320-325.
European Office Action dated Jul. 30, 2010.

*Primary Examiner* — Jeffrey G Hoekstra
(74) *Attorney, Agent, or Firm* — Andrus, Sceales, Starke & Sawall, LLP

(57) ABSTRACT

The invention relates to a method and apparatus for assessing the reactivity observable in a certain physiological signal, especially the EEG signal, of a comatose subject. In order to obtain an objective and a reliable measure of the reactivity automatically and without the presence of a trained EEG specialist, a time reference corresponding to a stimulus is detected and the physiological signal data obtained from the subject is aligned with the time reference. Two sets of values are determined for a measure indicative of the amount of irregularity in the physiological signal data, both sets including at least one value of the said measure and having defined positions with respect to the time reference in time domain. Based on the two sets, the apparatus determines whether reactivity is present in the physiological signal data.

12 Claims, 4 Drawing Sheets

MEASUREMENT OF EEG REACTIVITY

CROSS REFERENCE TO RELATED APPLICATION

The present application is a continuation-in-part of U.S. patent application Ser. No. 11/273,574, filed on Nov. 14, 2005 now U.S. Pat. No. 8,064,993.

FIELD OF THE INVENTION

The present invention relates to the assessment of the reactivity of the central nervous system of a patient to external stimulation as observable on/in a physiological signal, especially an EEG signal. Below, the reactivity observable on/in a physiological signal is termed physiological signal reactivity. If the physiological signal concerned is an EEG signal, the said reactivity is termed briefly EEG reactivity.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

While spontaneous variation in a wake-sleep cycle causes physiological and rapidly reversible changes in the EEG, different derangements of internal system homeostasis disturb the environment in which the brain operates, and therefore the function of the brain and the resulting EEG are disturbed. The EEG signal is a very sensitive measure of the neuronal derangements, which may reflect in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

Generally, if a patient is unconscious (without sedation), the reason in 30 to 40 percent of the cases is intracranial, whereas in 60 to 70 percent of the cases unconsciousness is due to hypoxic-ischaemic, metabolic, or toxic reasons. This kind of general unconsciousness is currently monitored with the help of the Glasgow Coma Scale (GCS). It defines the patient (un)consciousness by using three parameters: the best eye opening response, the best motoric response, and best response to speech. The final score represents the sum of the scores of the three categories. Table 1 below illustrates the Glasgow Coma Scale. Although the Glasgow Coma Scale is subjective and inter-rater variability may exist, it is the most widely used scoring system to assess patients with traumatic brain injury, for example.

TABLE 1

| The Glasgow Coma Scale | | |
| --- | --- | --- |
| Criterion | | Points |
| Eye Opening Response | Spontaneous | 4 |
| | Opens to verbal command | 3 |
| | Opens to pain | 2 |
| | None | 1 |
| Verbal response | Oriented | 5 |
| | Confused | 4 |
| | Inappropriate words | 3 |
| | Incomprehensible sounds | 2 |
| | None | 1 |
| Motor response | Obeys commands | 6 |
| | Localises pain | 5 |
| | Withdraws from pain | 4 |
| | Abnormal flexion | 3 |
| | Extends to pain | 2 |
| | None | 1 |
| Total | | 3–15 |

Diagnostically, the EEG is only rarely specific, since many systemic disorders of the brain produce similar EEG manifestations. However, an EEG signal may be of critical value, as it may differentiate between broad categories of psychogenic, epileptic, metabolic-toxic, encephalitic, and focal conditions, for example.

In a healthy sleeping subject, the EEG is reactive to various stimuli according to the sleep stages. For a comatose patient, a test of the reactivity of the EEG signal to external stimulation is an important assessment tool for a clinician, since it provides significant information regarding the state and outcome of the patient. EEG reactivity may reveal potentially treatable conditions and also provide information of the level of drug-induced sedation. While some conclusions about the probability of a recovery can be drawn from the raw EEG signal as such, it has been shown that reactivity of the EEG signal to stimulation, i.e. a detectable change in the EEG signal after a stimulus as compared to the pre-stimulus situation, is a more specific indicator of a favourable outcome, cf. G. B. Young, et al: *An Electroencephalographic Classification for Coma*, Can. J. Neurol. Sci. 1997; 24: 320-325. Therefore, testing the EEG reactivity is an essential part of the EEG examination of a comatose patient. Moreover, the test of EEG reactivity provides information regarding the state of a patient for whom the GCS or another observational scoring system is not applicable. This is the case, for example, when neuromuscular blocking agents have been administered to the patient, which makes the patient unable to respond and thus the observational scoring systems inapplicable.

At present, the EEG reactivity is assessed by an EEG specialist trained to interpret EEG waveforms. In practice, ICU (Intense Care Unit) doctors or nurses, who are skilled in making GCS-type assessments, are usually not capable of interpreting the EEG waveforms, and therefore a consulting EEG specialist has to be called in for the test of EEG reactivity. Various types of stimuli, such as auditory (shouting the patient's name, blowing a horn) and somatosensory (pinching the skin, squeezing nail beds, shaking) stimuli, may be applied in the test. The EEG specialist annotates the time instant of the stimulation and compares the recorded EEG signal before and after the annotated time instant. Often the EEG signal shows reactivity only to some of the given stimuli; in this case reactivity is considered to be present.

The test of the EEG reactivity is thus currently based on the visual assessment of the EEG waveform prior to and after the stimulation, since developing an automated testing procedure is complicated. This is mainly due to the high inter-patient variability, which may cause great variations between different patients both in the initial EEG signal waveforms and in the reactions to stimuli. The initial EEG signal waveforms, for example, may vary greatly depending on the state of the patient. The reactions that may be seen in the EEG signal after the stimulation comprise different types of responses, such as slow wave responses, voltage reduction and filtering of remnants of the basic rhythm, and flattening of voltage without or with blocking of slow waves, cf. Ernst Niedermayer, Fernando Lopes da Silva: Electroencephalography: basic principles, clinical applications, and related fields, p. 462, fourth edition, 1998, ISBN 0-683-30284-1. The visual assessment of the EEG is performed by a specialist, since he/she must understand the features of the EEG and take into account various patient-specific factors, such as the age, the level of drowsiness, and the metabolic state of the patient, as well as the possible disorders and their effect on the basic EEG signal.

Due to the above-described high variability between different patients, no automatic quantification tools exist for assessing the EEG reactivity, but a specialist is needed for the interpretation of the EEG waveforms. Consequently, the assessments are subjective and dependent on the level of expertise of the specialist. One possible source of the inter-individual variation in the EEG reactivity is the status of peripheral/sensory nervous system, which affects the transmission of the stimulus to the brain. The state of the sensory pathways may be affected by either medication or possible injury due to trauma or disease.

The present invention seeks to alleviate or eliminate the above-mentioned drawback and to devise an automated mechanism for evaluating EEG reactivity.

SUMMARY OF THE INVENTION

The present invention seeks to provide a novel mechanism for assessing the EEG reactivity of a patient, especially that of a comatose patient. The invention further seeks to provide a mechanism that provides an objective and a reliable measure of the EEG reactivity to be obtained automatically without the presence of a consulting EEG specialist.

The automated EEG reactivity measurement of the invention is based on the discovery that the various types of changes that may appear in the EEG signal in response to a stimulus are such that they cause a change in a measure which is indicative of the amount of irregularity in the EEG signal data, especially of the entropy of the EEG signal.

In the present invention, the EEG signal data obtained from a patient is aligned temporally with a stimulus that stimulates the patient. As discussed below, the stimulus may be generated in various ways either automatically by the apparatus of the invention or manually by the nursing staff. Furthermore, unintentionally produced stimuli, to which the patient is exposed in a clinical environment, may also be utilized. Two value sets are then determined, which represent the irregularity of the EEG signal data typically both prior and subsequent to the moment of the stimulus. Each set includes at least one but preferably a plurality of values for a measure indicative of the irregularity of the EEG signal data. Based on the two sets, the apparatus of the invention decides whether EEG reactivity is present. As discussed below, the decision-making may be based on a comparison of the deviations within and between the two value sets.

The stimulus may also be of a longer duration, in which case either or both of the value sets may include one or more values that represent the irregularity of the EEG signal during the stimulus. A time reference that indicates the position of the stimulus in time domain may thus indicate a time instant, a time interval, or several distinct time instants. The value sets determined thus have defined positions with respect to the time reference in time domain.

The reactivity of the central nervous system of the subject may also be determined with respect to another physiological signal than the EEG, such as the ECG.

Thus one aspect of the invention is providing a method for measuring the physiological signal reactivity of a subject. The method includes the steps of receiving physiological signal data obtained from a subject, applying a time reference corresponding to a stimulus, and aligning the physiological signal data temporally with the time reference. The method further includes the steps of deriving a first set of values for a first measure indicative of irregularity in the physiological signal data, the first set including at least one value of the first measure, producing a second set of values for the first measure, the second set being subsequent to the first set and including at least one value of the first measure, and determining, based on the first set and the second set, whether reactivity is present in the physiological signal data, wherein the first and second sets have defined positions with respect to the time reference in time domain.

Another aspect of the invention is that of providing an apparatus for measuring the physiological signal reactivity of a subject. The apparatus includes means for receiving physiological signal data obtained from a subject, means for applying a time reference corresponding to a stimulus, and alignment means for temporally aligning the physiological signal data with the time reference. The apparatus further includes first calculation means for deriving a first set of values for a first measure indicative of irregularity in the physiological signal data, the first set including at least one value of the first measure, second calculation means for producing a second set of values for the first measure, the second set being subsequent to the first set and including at least one value of the first measure, and third calculation means for determining, based on the first set and the second set, whether reactivity is present in the physiological signal data, wherein the first and second sets have defined positions with respect to the time reference in time domain.

The invention enables an objective and a reliable measure of the EEG reactivity to be obtained without the presence of an EEG specialist, which enhances patient monitoring in an ICU environment.

A further aspect of the invention is that of providing a computer program product by means of which known patient monitoring devices may be upgraded and thus their applicability extended to include the assessment of physiological signal reactivity. The program product includes a first program code portion configured to apply a time reference corresponding to a stimulus and to align physiological signal data obtained from a subject with the time reference, a second program code portion configured to derive a first set of values for a first measure indicative of irregularity in the physiological signal data, the first set including at least one value of the first measure, a third program code portion configured to produce a second set of values for the first measure, the second set being subsequent to the first set and including at least one value of the first measure, and a fourth program code portion configured to determine, based on the first and second sets, whether reactivity is present in the physiological signal data, wherein the first and second sets have defined positions with respect to the time reference in time domain.

In one preferred embodiment of the invention, the measurement employs transcranial magnetic stimulation (TMS) of the subject's cortex. Since the stimulus is in this case not sensed through the sensory nervous system, the state of the neural pathways does not affect the measurement, but the measurement is specific to the cortical state of the subject. Furthermore, TMS offers an opportunity to activate relatively large populations of cortical neurons, hence supplying in a way much stronger stimulation to the cortex than what would be possible through sensory stimulation. In this way, TMS provides an efficient tool for assessing different levels of deep sedation or unconsciousness.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 6 in the appended drawings, wherein.

DETAILED DESCRIPTION OF THE INVENTION

As discussed above, the present invention rests on the discovery that although various types of responses may appear in the EEG signal after a stimulus, the said responses are nevertheless such that they cause a change in the entropy of the EEG signal, or, more generally, in a measure indicative of the irregularity of the EEG signal. Therefore, the reactivity of the EEG may be quantified by measuring the change that stimulation causes in said measure.

Figure 1:
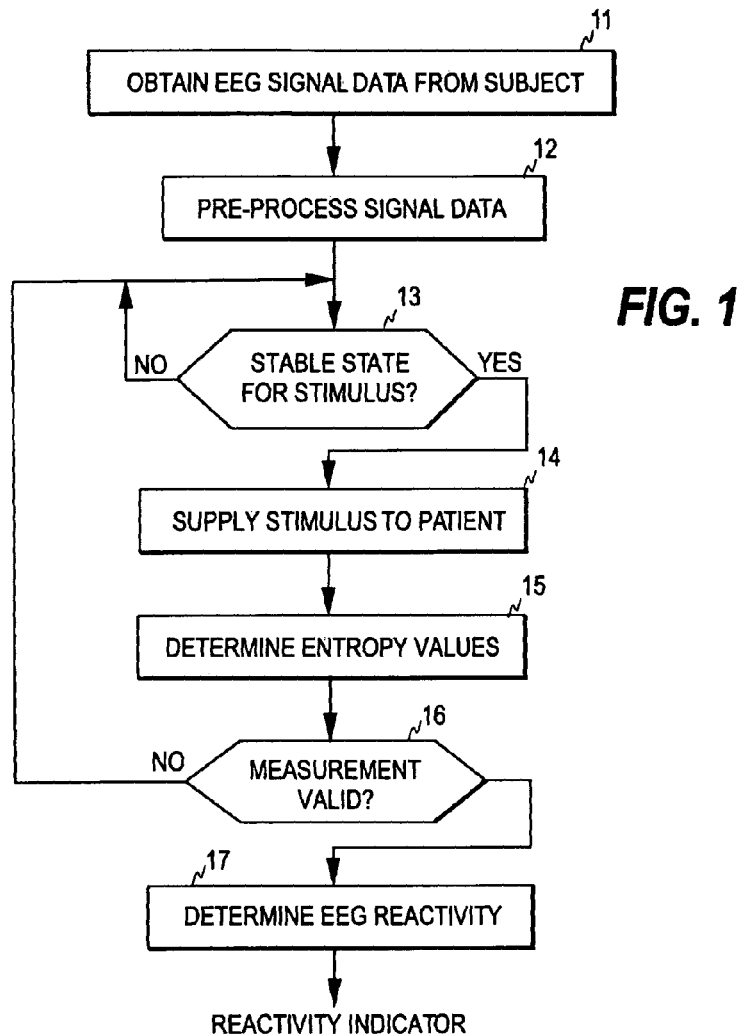
FIG. 1 is a flow diagram illustrating one embodiment of the method of the invention.

FIG. 1 illustrates one embodiment of the present invention. The EEG signal measured from a patient (step 11) is first digitized and the sampled EEG signal is filtered to exclude high- and low-frequency artifacts (step 12). As is common in the art, the digitized signal samples are processed as sets of sequential signal samples representing finite time blocks or time windows, commonly termed "epochs". The process may then monitor the incoming EEG signal data in order to detect a suitable moment for giving the stimulus (step 13). The purpose of this detection is to ensure that the EEG signal is stable enough prior to the application of the stimulus, i.e. that the signal does not include unwanted distortions when the stimulus is given.

When the EEG signal is stable enough, a stimulus is given (step 14). The stimulus signal may assume any suitable form and may thus be an electrical, a mechanical, an electromagnetic, or an auditory stimulus, for example. Moreover, the stimulus is preferably predetermined in the sense that the system knows the parameters defining the stimulus. A time label indicating the time instant of the stimulus is attached to the EEG signal data to indicate the moment of the stimulus in the data sequence. As also discussed below, in one embodiment of the invention the stimulus is not supplied through the sensory nervous system of the subject, thereby to prevent the actual cerebral state of the subject from being obscured by abnormally functioning neural pathways.

The response caused by the stimulus in the EEG signal is then detected by calculating entropy values in successive time windows both prior to and after the stimulus signal (step 15). In this example, entropy refers to spectral entropy. However, several other types of entropies may also be utilized, such as Shannon entropy or approximate entropy.

Based on the successive entropy values obtained from step 15, the process may then check whether the measurement is regarded as valid, i.e. whether the moment of the application of the stimulus was really a suitable moment for the measurement (step 16). If this is the case, the process calculates a measure indicative of the EEG reactivity of the subject (step 17). In the opposite case, the process returns to step 13 to detect a suitable moment to repeat the stimulation.

Figure 2:
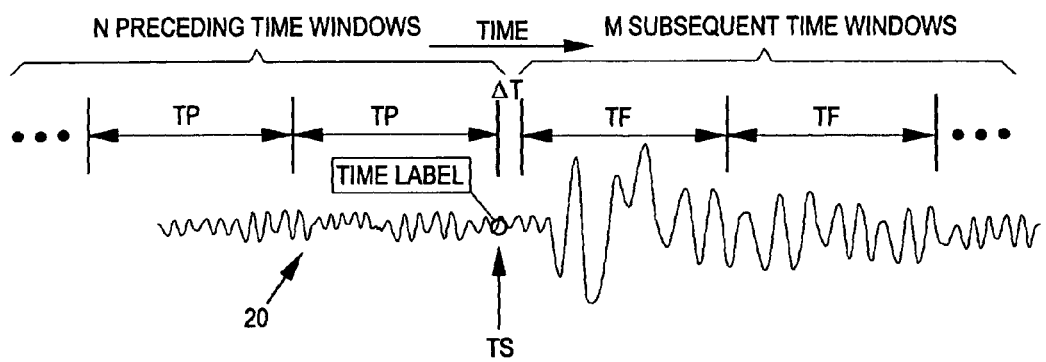
FIG. 2 illustrates the time windows used for determining the EEG reactivity.
Figure 3:
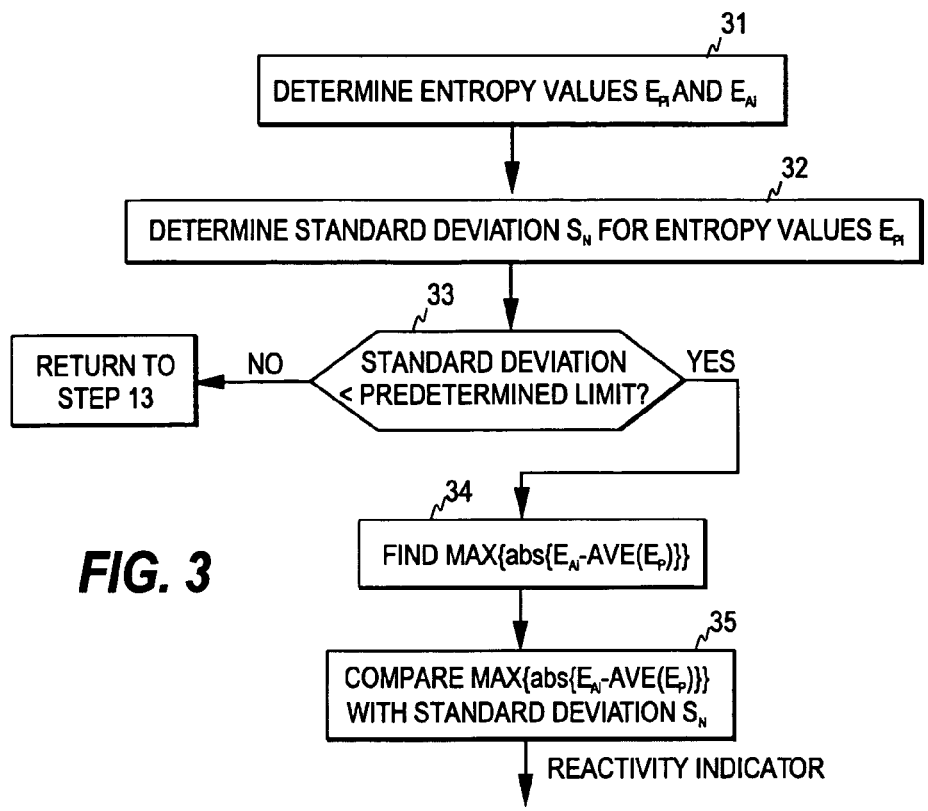
FIG. 3 is a flow diagram illustrating one embodiment for the reactivity determination in the embodiment of FIG. 1.

Steps 15 to 17 of FIG. 1 are now discussed in more detail with reference to FIGS. 2 and 3. FIG. 2 shows an EEG signal 20 obtained from the patient, together with a time line showing the time windows used to determine the entropy of the signal. FIG. 3 in turn is a flow diagram illustrating one embodiment of the reactivity determination performed in steps 15 to 17. In FIG. 2, the stimulus signal is given at time instant TS. To align the EEG signal temporally with the stimulus signal, the apparatus/system of the invention may attach a time label to the EEG signal to indicate the time instant of the stimulus signal. The apparatus/system of the invention then calculates the entropy values of the EEG signal data within N time windows TP that precede the moment of the stimulus and within M time windows TF that follow the moment of the stimulus. The length of one time window may be of the order of a few seconds, such as 4 seconds. The total length of the time covered by the N time windows may be of the order of 12 sec to 1 minute, such as 24 seconds. The same applies to the total length of the time covered by the M time windows. Therefore, M may equal N. If this is the case and the above typical values are used, the apparatus/system of the invention thus calculates 12 entropy values of which 6 represent the entropy of the EEG signal before the stimulus signal and 6 the entropy of the EEG signal after the stimulus signal. Although the entropy of the EEG signal is typically determined in a plurality of time windows both prior and subsequent to the stimulus, in an extreme case M and/or N may equal one.

Consequently, in step 15 of FIG. 1, the system first calculates N entropy values $E_{Pi}$ (i=1, ..., N), which indicate the entropy of the EEG signal in N consecutive time windows prior to the stimulus, and M entropy values $E_{Ai}$ (i=1, ..., M), which represent the entropy of the EEG signal in M consecutive time windows after the stimulus. This is denoted with step 31 in FIG. 3. A short guard period (safety margin) ΔT shown in FIG. 2 may be used after the stimulus to eliminate the interference that the stimulation, such as electrical stimulation, may cause in the EEG signal. The length of the guard period depends on the type of the stimulus.

Based on the entropy values, the apparatus/system may then calculate the standard deviation $S_N$ for the N entropy values $E_{Pi}$ (step 32 in FIG. 3). The standard deviation obtained may then be compared with a predetermined limit value to ensure that the measurement is valid (step 33). If the standard deviation is smaller than a predetermined limit value, the process decides that the measurement conditions are stable enough and the measurement is valid. Other criteria may also be applied to ensure, for example, that there are no external sources of interference present.

If the conditions are sufficiently stable, the process first calculates the entropy value $E_{Ai}$ within each of the M time windows following the moment of the stimulus and the average entropy $AVE\{E_P\}$ of the N time windows preceding the stimulus. The process then finds the time window with the maximum deviation $MAX\{abs\{EAi-AVE\{E_P\}\}\}$ from among the M time windows following the stimulus, where $abs\{E_{Ai}-AVE\{E_P\}\}$ stands for the absolute value of $E_{Ai}-AVE\{E_P\}$. The maximum deviation is thus determined as compared to the average entropy calculated. The process then compares the said maximum deviation with the standard deviation $S_N$ calculated (steps 34 and 35). If the maximum deviation obtained is high enough as compared to the standard deviation $S_N$, EEG reactivity is detected. The comparison may involve the calculation of the difference or the ratio of the said two values and the difference or the ratio may be compared with a predetermined threshold value to decide whether EEG reactivity is found.

The system then outputs an indicator of the reactivity. This indicator may simply be a notification indicating whether or not EEG reactivity was detected. If EEG reactivity is detected, the value of the reactivity may also be output. The value may be, for example, the above maximum deviation $MAX\{abs\{EAi-AVE\{E_P\}\}\}$. Furthermore, the value of the reactivity may further be scaled to a fixed range, such as between 0 and 100, using an appropriate scaling function.

Alternatively, the calculation of the standard deviation $S_N$ for the N entropy values $E_{Pi}$ (i=1, ..., N) may be omitted and the maximum deviation within the M time windows may be compared with a constant threshold value.

Instead of different types of entropies, the evaluation of the EEG reactivity may also be based on another parameter that is related to the amount of irregularity in the EEG signal data measured from the patient. Other possible quantifications that may be used include fractal spectrum analysis, Lempel-Ziv complexity, or spectral, bispectral, multispectral or stationarity analyses. For example, a relative increase of a peak in a spectrum causes a decrease of irregularity of the signal and can thus be used for the determination of EEG reactivity.

As discussed above, the stimulus may assume various forms. Furthermore, the time instant of the stimulus may be aligned with the EEG signal in a plurality of ways:

1. The monitoring device may generate the stimulus, such as a TOF (Train of Four) electric stimulus. The monitoring device attaches one or more time labels to the EEG signal data, which indicate the time instant of the stimulus signal.
2. The user may give the stimulus and indicate the corresponding moment to the monitoring device. The user may, for example, push a button when giving the stimulus. The monitoring device attaches a time label to the EEG signal data, which corresponds to the time instant indicated by the user.
3. The monitoring device may detect the stimulus given by the user. For example, the user may generate a particular audio signal, which the monitoring device detects. The monitoring device attaches one or more time labels to the EEG signal data, which indicate the time instant of the stimulus signal detected.
4. The monitoring device may prompt the user to give a particular stimulus. The temporal alignment of the EEG and stimuli may be carried out in one of the above ways.

If the monitoring device generates the stimulus, it may assess the EEG reactivity repeatedly by applying at least one stimulus at regular intervals, e.g. every 30 minutes. In this way, the EEG reactivity may be monitored continually. The monitoring device may then keep track of the trend of the EEG reactivity and display it graphically.

In one embodiment of the invention, step 13 may be omitted, since the validity of the measurement is checked after the stimulus signal is given. However, performing the check of step 13 may decrease the number of unnecessary stimuli.

Figure 4B:
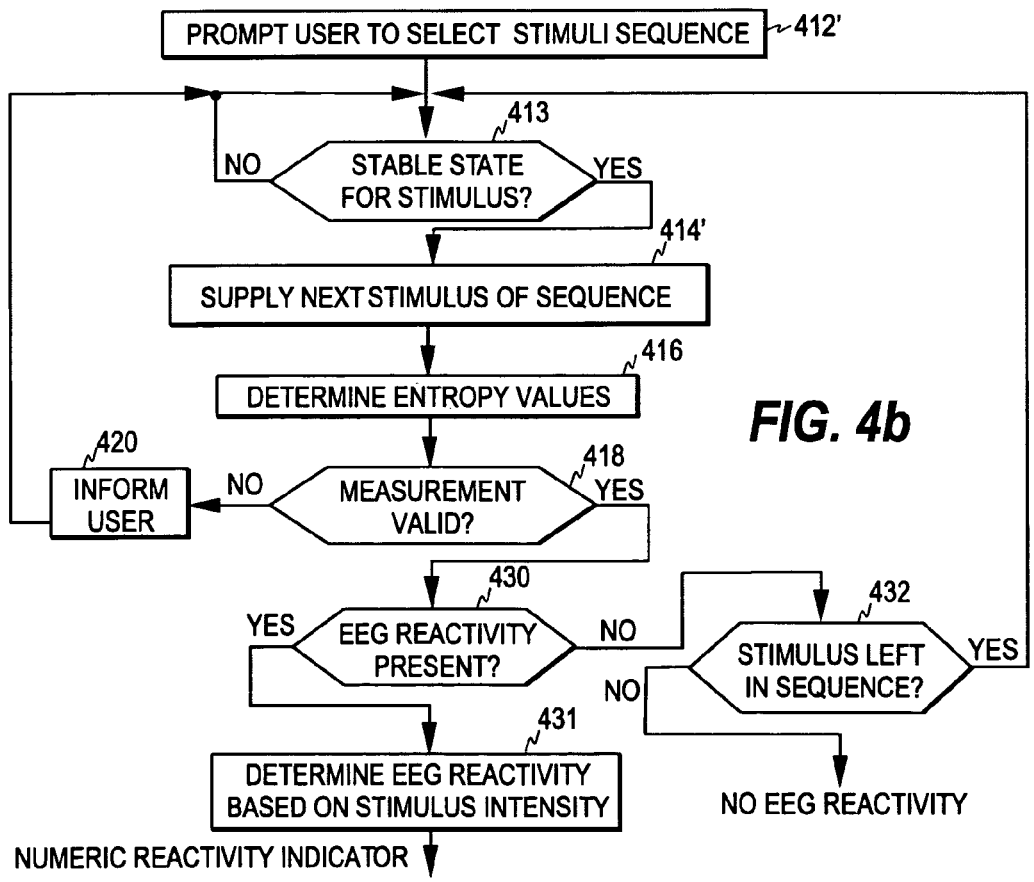
FIG. 4b is a flow diagram illustrating still another embodiment of the method of the invention.
Figure 4A:
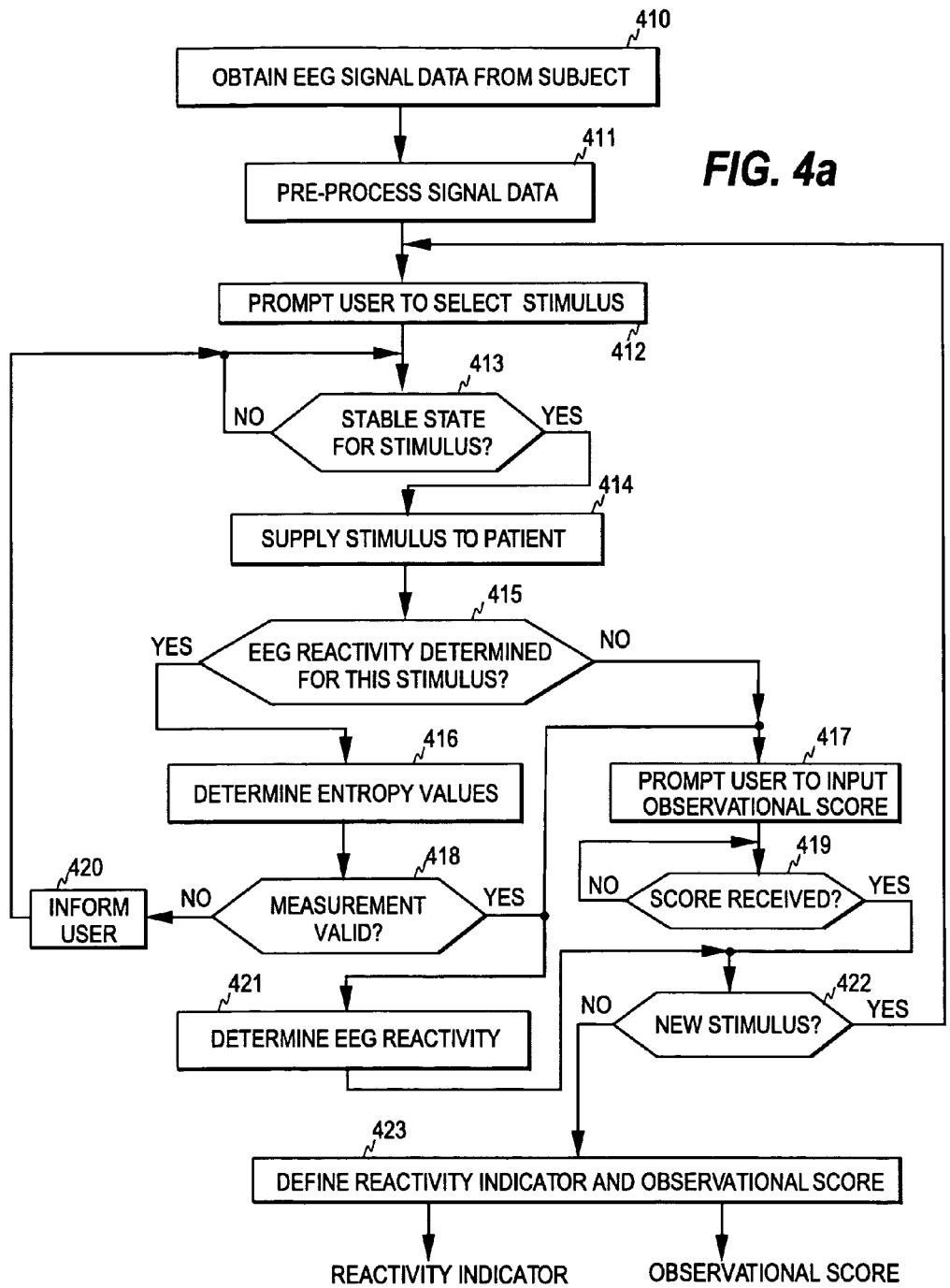
FIG. 4a is a flow diagram illustrating another embodiment of the method of the invention.

In a further embodiment of the invention, which is illustrated in FIG. 4a, the determination of the EEG reactivity is combined with another GCS-type scoring system, which the user may perform with the assistance of the monitoring device of the invention. The said another scoring system may be any other observational scoring system in which the user, such as an ICU doctor or nurse, examines the external responses of the patient. In this example, the observational scoring system utilizes the following four types of stimuli: a vocal stimulus, a noisy stimulus, a TOF stimulus, and a tetanic stimulus. The stimuli are used in the above-mentioned ascending order of intensity and if no observable response is obtained to a certain stimulus, the process proceeds to use the next stimulus.

In this embodiment, the first steps 410 and 411 correspond to steps 11 and 12 of the embodiment of FIG. 1. As the observational scoring system involves the use of four types of stimuli in ascending order of intensity, the user first selects the least intense stimulus signal, which is in this example a standardized "open your eyes" command supplied from a sound record. Since the order of the stimuli is fixed, the apparatus may also pre-select the stimuli and prompt for user confirmation on the selection made (step 412).

The monitoring device then monitors the incoming EEG signal data in order to detect a suitable moment (step 413) and gives the stimulus if the EEG signal is stable enough. These steps correspond to steps 13 and 14 of FIG. 1. In this example, the stimulus may be supplied through patient headphones.

The monitoring device may then check whether the stimulus signal given is such that also the EEG reactivity may be determined based on it (step 415). All stimulus signals selected by the user are not necessary suitable for determining the EEG reactivity, wherefore the monitoring device calculates the entropy values only if the stimulus given is suitable for this purpose. If a suitable stimulus was applied, the monitoring device calculates the entropy values corresponding to the time windows in the above-described manner and checks whether the measurement is regarded as a valid measurement (steps 416 and 418). These steps correspond to steps 15 and 16 in the embodiment of FIG. 1. If the measurement is regarded as valid, the process calculates a measure indicative of the EEG reactivity of the subject (step 421) and prompts the user to input the score for the observational scoring system (step 417). Upon receiving the score from the user, the monitoring device prompts whether the user wishes to continue by giving a new stimulus (step 422). If so, the process jumps back to step 412 and the user is prompted to select or confirm the next stimulus (step 412). In this example, the next stimulus is a noisy stimulus consisting of standardized noise bursts, which may be supplied through the said patient headphones.

If any of the selected stimuli is not appropriate for determining the EEG reactivity, the process jumps from step 415 directly to step 417, i.e. for such a stimulus the apparatus stores only the observational score given by the user.

In the above-described manner, the user may utilize the monitoring device to give the stimuli needed to obtain the scores for any observational scoring system. Based on each appropriate stimulus, the monitoring device may also determine the EEG reactivity (step 421). When the user has finished scoring the subject, he/she indicates that no more stimuli are needed (step 422/yes). After this, the monitoring device determines the total score of the observational scoring system and the reactivity indicator (step 423). The final reactivity indicator may provide the values of reactivity for each stimulus type individually, or it may indicate, for example, the average of the EEG reactivity values obtained. In case the reactivity indicator indicates the presence/absence of EEG reactivity without any numeric values, the monitoring device may decide that EEG reactivity is present if at least one of steps 421 indicates its presence.

If it is detected at step 418 that the measurement is not valid, the monitoring device informs the user of the situation (step 420) and returns to step 413 to detect a suitable moment to repeat the stimulus.

Instead of a standardized scoring system any subset or modified set of stimuli may be used. The apparatus/system of the invention may be provided with means for giving the user a possibility to pre-configure a particular set of stimuli that are prompted in a predetermined order. It is advantageous that a stimulus of lower intensity precedes a stimulus of higher intensity so that if a response is observed at a particular level of intensity the process may be stopped to avoid unnecessary interference of the patient. Pre-configured stimuli sequences, which the said sets may form, may also be utilized so that the apparatus/system of the invention starts with the least intense stimulus and automatically proceeds to the next stimulus of the sequence, if no response is detected to the stimulus just given. In this embodiment, the apparatus thus determines the need of a further stimulus and then gives the said stimulus without user input if the need exists.

In the above embodiments, the indicator of EEG reactivity indicates either the presence/absence of EEG reactivity or a numeric value obtained based on the change in the irregularity of the EEG signal data. However, in a further embodiment of the invention, which is illustrated in FIG. 4b, a numeric value may be obtained even though the presence/absence of EEG reactivity is still determined similarly, i.e. in an on/off-manner. This is accomplished so that the intensity of the stimulus determines the numeric value of the EEG reactivity: the less intensive the stimulus required to produce reactivity detection, the higher the value of EEG reactivity, and vice versa. When combined with the above-mentioned pre-configured stimuli sequences, this embodiment may be used to automatically produce a score similar to that of the commonly used observational scoring systems, such as the GCS or the Ramsay scoring system. In FIG. 4b, corresponding steps have been denoted with the same reference numerals as in FIG. 4a, while modified steps are provided with an apostrophe. Steps 410 and 411 are omitted in FIG. 4b. In the embodiment of FIG. 4b, the user thus first selects one of the pre-configured stimuli sequences (step 412') and the apparatus first supplies the least intensive stimulus of the sequence selected (step 414'). If it is detected at step 430 that reactivity is present, the apparatus determines the numeric value of the reactivity based on the intensity of the stimulus given (step 431). If reactivity is not detected and there is still at least one stimulus available in the sequence, the apparatus proceeds to give the next stimulus in the sequence (step 432). In this embodiment, all the stimuli are intended for the determination of the EEG reactivity, wherefore check 415 is not needed.

The above automatic scoring system of the invention may be used to extend the commonly used observational scoring systems to cover deep sedation levels, i.e. patients that no more have observable responses.

The stimulus may also be of a longer duration and at least some of the values of the measure indicative of the irregularity of the EEG signal data may be determined during the stimulus. For example, the intensity of the stimulus may increase slowly, which allows the first value set to be determined either prior to or during the stimulus. The second value set may then be determined during or after the stimulus. The sets and the stimulus may also overlap in time domain; the first set may include values indicative of the irregularity prior to and during the stimulus, while the second set may include values indicative of the irregularity during and after the stimulus.

In the above embodiments, the measurement is generally indicative of the reactivity of the central nervous system of a patient to external stimulation. However, if desired, the measurement may also be made specific to the cortical state only. In such an embodiment, magnetic stimulation of the cortex may be employed to avoid a situation in which damaged neural pathways within the sensory nervous system or between the sensory nervous system and the cortex may obscure the real cortical state of the patient. In transcranial magnetic stimulation (TMS), with the help of at least one coil placed on the head, the cerebral cortex can be stimulated without health risks and pain by applying a strong magnetic field, advantageously with a duration of 50-500 µs, that induces an electric current at a desired point. The induced current activates a group of cortical neurons. Hence, direct magnetic stimulation of the cortex can be used as a stimulus when testing the EEG reactivity. Furthermore, TMS provides an efficient tool for assessing deep levels of sedation or unconsciousness, since TMS stimulation may be relatively stronger stimuli than the stimuli sensed through the sensory nervous system.

Thus, in an embodiment employing magnetic stimulation, the stimulating system comprises at least one coil and a current source connected to the coil(s). The current source is configured to supply a current pulse to the coil(s), which may be placed by the nursing staff on or above the vertex of the head of the patient to stimulate the patient's cortex directly. Since magnetic stimulation of the cortex is known as such, the stimulating system is not discussed in detail in this context. The stimulating system may be similar to the one disclosed in U.S. Pat. No. 6,256,531, for example, which discloses a method and apparatus for mapping cortical connections.

Since the stimulus is in this embodiment not supplied through the sensory nervous system of the subject, the state of the sensory nervous system cannot affect the measurement, but the measurement is specific to the cortical state only.

The above embodiments may also be combined so that a measurement employing at least one stimulus sensed through the sensory nervous system is performed first. Depending on the situation, a further measurement employing magnetic stimulation of the cortex may be performed after the first measurement. The further measurement may be performed, for example, if the first measurement indicates low reactivity, thereby to test the state of the sensory nervous system. Alternatively, the further measurement may be performed regardless of the result of the first measurement, to verify the result of the first measurement.

Figure 5:
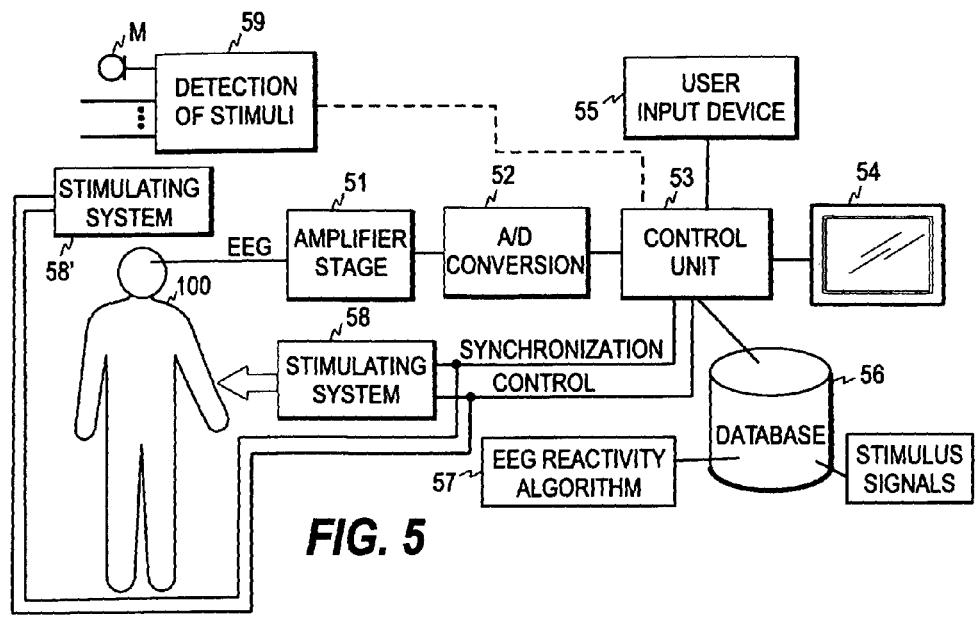
FIG. 5 illustrates one embodiment of the apparatus/system of the invention.

FIG. 5 illustrates one embodiment of the system or apparatus according to the invention. The EEG signal data obtained from electrodes applied to the forehead of a patient 100 is supplied to an amplifier stage 51, which amplifies the signal(s) before they are sampled and converted into digitized format in an A/D converter 52. The digitized signals are supplied to a control unit 53 which may comprise one or more computer units or processors.

The computer unit is provided with a memory or database 56 holding the digitized signal data obtained from the electrodes. The memory or database may also store one of the EEG reactivity algorithms 57 described above in FIGS. 1 to 4b. The control unit executes the stored algorithm, whereby a measure of the EEG reactivity is obtained as disclosed in connection with FIGS. 1 to 4b. Various data needed by the algorithm, such as the reactivity values that correspond to the stimuli, may be pre-stored in the memory or the algorithm may calculate such data.

The reactivity indicator, its trend, and the above-described user notifications may be displayed on the screen of a monitor 54, which forms part of the user interface of the device. Although a control unit comprising one computer unit or one processor may perform the above steps, the processing of the data may also be distributed among different units/processors (servers) within a network, such as a hospital LAN (local area network). The apparatus of the invention may thus also be implemented as a distributed system.

The monitoring device may further be provided with one or more stimulator units 58, 58' for giving the stimuli. As discussed above, the stimulus generated by the stimulator unit may assume many forms and the stimulus signals may be aligned with the EEG signal in various ways. The characteristics of the available stimuli may be stored in the memory 56. The system may comprise one unit 58 for generating stimuli sensed through the sensory nervous system and another unit 58' for generating electromagnetic stimulus pulses. Preferably, all the stimulators form an integrated whole with the EEG device being either integrated parts of it or plug-in modules.

The user may control the operation of the monitoring device through a user input device 55, such as a keyboard. The computer or control unit 53 controls the stimulator unit according to the commands given by the user from the user input device.

In the above embodiments, the stimulus/stimuli is/are produced intentionally to assess the EEG reactivity. However, the apparatus of the invention may also monitor the clinical environment to detect the natural stimuli occurring therein. The natural stimuli may be originated from various sources, and one or more such sources may be monitored by a monitoring unit 59 shown in FIG. 5. For example, the noise level may be recorded through a microphone M, and the indicator of EEG reactivity may be determined when a noise peak of sufficient amplitude is detected. Thus, in this embodiment no stimulation unit is needed but the natural stimuli occurring in the environment are monitored. By continually determining the responses to the natural stimuli, the apparatus may keep track of the changes in the EEG reactivity of the patient.

A conventional patient monitor intended for measuring the level of consciousness may also be upgraded to enable the monitor to determine the EEG reactivity of a patient.

Such an upgrade may be implemented by delivering to the monitoring device a plug-in software module that enables the device to calculate the reactivity based on the time series of the EEG signal data stored in the device. The software module may be delivered, for example, on a data carrier, such as a CD or a memory card. The software-based upgrade may be such that it supports the manual stimulus indication given by the user through a user input device of the patient monitor, in which case no stimulus unit is needed in the monitor.

Figure 6:
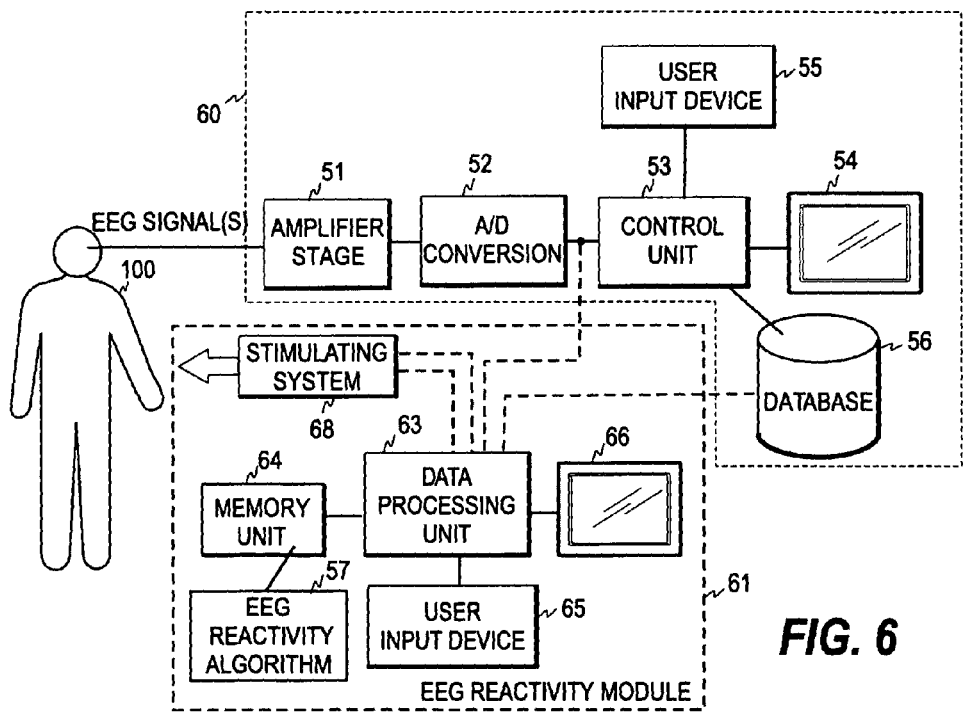
FIG. 6 illustrates another embodiment of the apparatus of the invention.

The upgrade may also be implemented as a separate monitoring module connectable to a conventional patient monitor intended for measuring the level of consciousness. As is shown in FIG. 6, such a module 61 may comprise a data processing unit 63 which receives the time series of the EEG signal data from a conventional patient monitor 60 and derives the EEG reactivity from the said data. Therefore, the conventional monitor does not necessarily have to be an entropy-based monitor.

The reactivity module 61 may optionally include the above-described stimulator unit 68, especially if the conventional monitor to which the module is connectable is not provided with such a unit. However, as is obvious from the above, a stimulator unit is not necessarily needed in the EEG reactivity module even if the conventional monitor failed to have any stimulation means. Namely, the user may give the stimulus signal manually, using a horn, for example, and indicate the moment of the stimulus signal through the user interface of the module. The user may, for example, press a certain button simultaneously when he/she gives the stimulus signal. The EEG reactivity module may further comprise a display of its own for displaying the reactivity indicators to the user.

Above, the invention was employed for assessing the EEG reactivity of a patient. However, depending whether a test of the reactivity of another physiological signal than the EEG provides valuable information about the patient, the same mechanism may be used in connection said another physiological signal. Therefore, the invention is not necessarily limited to the context of EEG.

Although the invention was described above with reference to the examples shown in the appended drawings, it is obvious that the invention is not limited to these, but may be modified by those skilled in the art without departing from the scope of the invention.

The invention claimed is:

1. An apparatus for assessing physiological signal reactivity of a subject, the apparatus comprising:
    a control unit for receiving physiological signal data obtained from a subject;
    a stimulating system in communication with the control unit, wherein the stimulating system supplies a time reference corresponding to a stimulus generated by the stimulating system;
    wherein the control unit is programmed to carry out the steps of:
    temporally aligning the physiological signal data with the time reference;
    deriving a first set of values for a first measure indicative of irregularity in the physiological signal data occurring before the time reference in the time domain, the first set including at least one value of the first measure;
    producing a second set of values for the first measure, the second set being subsequent to the first set and after the time reference in the time domain and including at least one value of the first measure; and
    determining, based on a comparison between the first set and the second set, whether reactivity is present in the physiological signal data.

2. An apparatus according to claim 1, wherein the control unit is configured to receive EEG signal data from the subject.

3. An apparatus according to claim 1, wherein the stimulating system is configured to apply a time instant corresponding to the stimulus.

4. An apparatus according to claim 3, wherein the control unit is programmed to define N consecutive time windows preceding the time instant and to determine the first measure for each of the N time windows, thereby to obtain N values of the first measure for the first set; and the control unit is programmed to define M consecutive time windows subsequent to the time instant and to determine the first measure for each of the M time windows, thereby to obtain M values of the first measure for the second set.

5. An apparatus according to claim 4, wherein the control unit is programmed to determine a second measure indicative of a standard deviation of the N values of the first measure, a third measure indicative of an average of the M values of the first measure, and a fourth measure indicative of a maximum deviation of the M values from the average;

the control unit is programmed for comparing the fourth measure with the second measure and generating a reactivity indicator indicating whether reactivity is detected in the EEG signal data.

6. An apparatus according to claim 4, wherein the control unit is further configured to determine a second measure indicative of an average of the M values of the first measure, and a third measure indicative of a maximum deviation of the M values from the average; and the control unit compares the third measure with a predetermined limit value and generates a reactivity indicator indicating whether reactivity is detected in the physiological signal data.

7. An apparatus according to claim 5, wherein the control unit is configured to generate a numeric value for the reactivity indicator.

8. An apparatus according to claim 6, wherein the control unit is configured to generate a numeric value for the reactivity indicator.

9. An apparatus according to claim 1, further comprising an input device operable to prompt a user to rate subject response based on the stimulus.

10. An apparatus according to claim 1, further including a detection device operable to define an intensity of the stimulus, and wherein the control unit is configured to determine a numeric reactivity value based on the intensity.

11. An apparatus according to claim 1, wherein the stimulation device is configured to include an electromagnetic pulse in the interior of the subject's head.

12. An apparatus according to claim 1, wherein the stimulation is sensed by the subject's sensory nervous system.

* * * * *